(12) United States Patent
Glazer et al.

(10) Patent No.: US 7,078,389 B2
(45) Date of Patent: *Jul. 18, 2006

(54) CHEMICALLY MODIFIED OLIGONUCLEOTIDE FOR SITE-DIRECTED MUTAGENESIS

(75) Inventors: Peter M. Glazer, Guilford, CT (US); Pamela A. Havre, New Haven, CT (US)

(73) Assignee: Yale University, New Haven, CT (US)

( * ) Notice: Subject to any disclaimer, the term of this patent is extended or adjusted under 35 U.S.C. 154(b) by 882 days.

This patent is subject to a terminal disclaimer.

(21) Appl. No.: 09/783,338

(22) Filed: Feb. 14, 2001

(65) Prior Publication Data

US 2002/0028922 A1  Mar. 7, 2002

Related U.S. Application Data

(63) Continuation of application No. 08/083,088, filed on Jun. 25, 1993, now abandoned.

(51) Int. Cl.
*A01N 43/04* (2006.01)
*C12Q 1/68* (2006.01)

(52) U.S. Cl. ............... 514/44; 435/6; 435/440; 435/443; 435/444; 435/455; 435/471

(58) Field of Classification Search ............ 435/6, 435/440, 443, 444, 455, 471; 514/44; 935/77, 935/78
See application file for complete search history.

(56) References Cited

U.S. PATENT DOCUMENTS 6,303,376 B1 * 10/2001 Glazer .................. 435/440

FOREIGN PATENT DOCUMENTS

EP  0 226 099  5/1988
EP  0 375 408  6/1990

OTHER PUBLICATIONS

Puri et al, "Targeted gene knockout by 2'-O-aminoethyl modified triplex forming oligonucleotides", J. Biol. Chem. (2001) 276(31):28991-28998.*
Lin et al, "Stability of DNA triplexes on shuttle vector plasmids in the replication pool in Mammalian cells", J. Biol. Chem. (2000) 275(50):39117-39124.*
Beal, et al., "Second Structural Motif for Recognition of DNA by Oligonucleotide-Directed Triple-Helix Formation," *Science* 251:1360-1363 (1991).
Beal, et al., "The Influence of Single Base Triplet Changes on the Stability of Pur-Pur-Pyr Triple Helix Determined by Affinity Cleaving," *Nuc. Acids Res.* 11:2773 (1992).
Blume, et al., "Triple Helix Formation by Purine-Rich Oligonucleotides Targeted to the Human Dihydrofolate Reductase Promoter," *Nucleic Acids Rec.* 20:1777 (1992).
Cooney, "Site-Specific Oligonucleotide Binding Represses Transcription of the Human c-myc Gene in Vitro," *Science* 241:456 (1998).
Durland, "Binding of Triple Helix Forming Oligonucleotides to Sites in Gene Promoters," *Biochemistry* 30:9246 (1991).
Duval-Valentin, et al., "Specific Inhibition of Transcription by Triple-Helix-Forming Oligonucleotides," *Proc. Natl. Acad. Sci. USA* 89:504 (1992).
Francois, "Sequence-Specific Recognition and Cleavage of Duplex DNA via Triple-Helix Formation by Oligonucleotides Covalently Linked to a Phenanthroline-Copper Chelate," *Proc. Natl. Acad. Sci. USA* 86:9702 (1989).
Gasparro, et al., "Site-specific targeting of Psoralen Photoadducts with a Triple Helix-Forming Oligonucleotide: Characterization of Psoralen Monoadduct and Crosslink Formation," *Nucleic Acids Research*, 22(14):2845-2852 (1994).
Giovannangeli, et al., "Oligodeoxynucleotide-directed photo-induced cross-linking of HIV proviral DNA via triple-helix formation," *Nucleic Acids Res.* 20:4275-4281 (1992).
Glazer, et al., "Detection and Analysis of UV-induced Mutations in Mammalian Cell DNA Using A Phage Suttle Vector," *Proc. Natl. Acad. Sci.* 83:1041-1044 (1986).
Grigoriev, et al., "A Triple-Helix-Forming Oligonucleotide-Intercalator Conjugate Acts as a Transcriptional Repressor via Inhibition of NF $_k$B Binding to Interleukin-2 Receptor α-Regulatory Sequence," *J. of Biological Chem.* 267:3389 (1992).

(Continued)

Primary Examiner—Jeffrey Fredman
(74) Attorney, Agent, or Firm—Pabst Patent Group LLP

(57) ABSTRACT

A mutagenic, triplex-forming oligonucleotide and methods for use thereof wherein the oligonucleotide is chemically modified to incorporate a mutagen and forms a triple-stranded nucleic acid molecule with a specific DNA segment of a target DNA molecule. Upon formation of the triplex, the mutagen is brought into proximity with the target molecule and causes a mutation at a specific site therein. The mutation activates, inactivates or alters the activity and function of the target molecule.

9 Claims, 9 Drawing Sheets

OTHER PUBLICATIONS

Grigoriev, et al., "Inhibition of Gene Expression by Triple Helix-directed DNA Cross-linking at Specific Sites," *Proceedings of the National Academy of Sciences of USA*, 90(8):3501-3505 (1993).

Havre, et al., "Targed Mutagenesis of DNA Using Triple Helix-forming Oligonucleotides Linked to Psoralen," *Proc. Natl. Acad. Sci. USA*, 90(16):7879-7883 (1993).

Ito, et al., "Sequence-Specific DNA Purification by Triplex Affinity Capture," *Proc. Natl. Acad. Sci. USA* 89:495 (1992).

Lin, et al., "Use of EDTA Derivatization to Characterize Interactions Between Oligodeoxyribonucleoside Methylphosphonates and Nucleic Acids," *Biochemistry* 28:1054 (1989).

Maher, et al., "Analysis of Promoter-Specific Repression by Triple Helical DNA Complexes in a Eukarvotic Cell-Free Transcription System," *Biochemistry* 31:70 (1992).

Maher, et al., *Science* 245:725 (1989).

Mergny, et al., "Sequence Specificity in Triple-Helix Formation: Experimental and Theoretical Studies of the Effect of Mismatches on Triplex Stability," *Biochemistry* 30:9791 (1991).

Mirabelli, et al., "In Vitro and in vivo pharmacologic activities of antisense oligonucleotides," *Anticancer Design* 6:647-661 (1991).

Moser, et al., "Sequence-Specific Cleavage of Double Helical DNA by Triple Helix Formation," *Science* 238:645 (1987).

Orson, et al., "Oligonucleotide Inhibition of IL2Rα mRNA Transcription by Promoter Region Collinear Triplexed Formation in Lymphocytes," *Nucleic Acids Res.* 19:3435 (1991).

Pei, "Site Specific Cleavage of Duplex DNA by a Semisynthetic Nuclease via Triple-Helix Formation," *Proc. Natl. Acad. Sci. USA* 87:9858 (1990).

Perrouault, et al., "Sequence-Specific Artificial Photo-induced Endonuclease Based on Triple Helix-Forming Oligonucleotides," *Nature* 344:358 (1990).

Postel, et al., "Evidence that a Triple-Forming Oligodeoxyibonucleotide Binds to the *c-myc* Promoter in HeLa Cells, Thereby Reducing *c-myc* mRNA Levels," *Proc. Natl. Acad. Sci. USA* 88-8227 (1991).

Posvic, et al., "Sequence-Specific Ikylation of Double Helical DNA by Oligonucleotide Directed Triple-Helix Formation," *J. Am. Chem. Soc.* 112:9428 (1992).

Praseuth, et al., "Sequence-Specific Binding and Photocrosslinking of a α and β Oligodeoxynucleotides to the Major Groove of DNA via Triple-Helix Formation," *Proc. Natl. Acad. Sci. USA* 85:1349 (1988).

Strobel, "Site-Specific Cleavage of Human Chromosome 4 Mediated by Triple-Helix Formation," *Science* 254:1639 (1991).

Takasugi, et al., "Sequence-specific Photo-Induced Cross-Linking of the Two Strands of Double-Helical DNA by a Psoralen Covalently Linked to a Triple Helix Forming Oligonucleotide," *Proceedings of the National Academy of Sciences of USA* 88(13:5602-5606 (1991).

Uhlman, et al., "Antisense Oligonucleotides: A New Therapeutic Principle," *Chem. Reviews* 90(4):544-584 (1990).

Wood, et al., "The Effect of Volume and Temperature on the Energy and Entropy of Pure Liquids," *J. Am. Chem. Soc.* 79:2023 (1957).

Young, "Triple Helix Formation Inhibits Transcription Elongation *in vitro*," *Proc. Natl. Sci. USA* 88:10023 (1991).

* cited by examiner

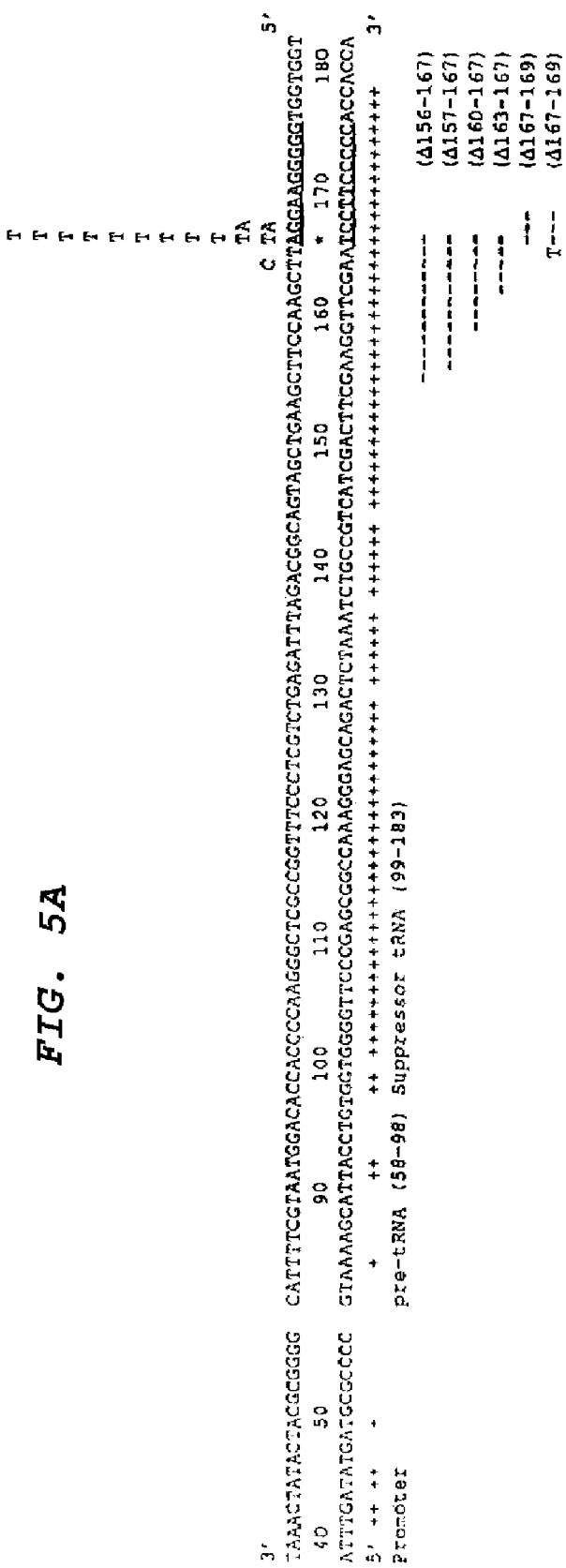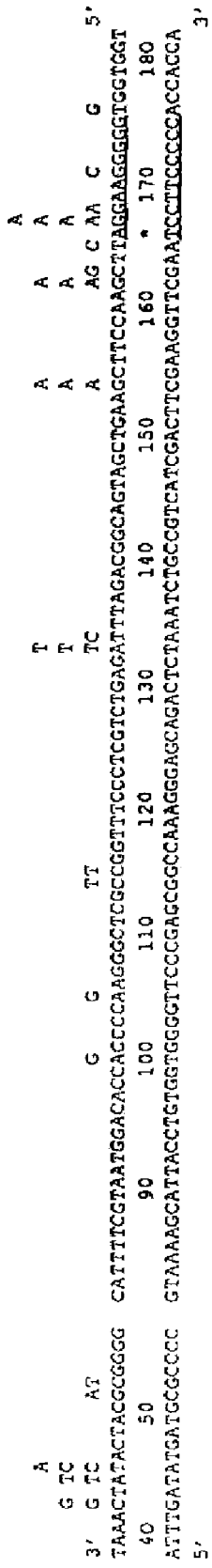
FIG. 5A
FIG. 5B

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: misc_feature
      (B) LOCATION: 1..11
      (D) OTHER INFORMATION: /function= "N is
         4'-hydroxymethyl-4,5',8-trimethylpsoralen"

(x) PUBLICATION INFORMATION:
            (A) AUTHORS: Glazer, Peter M.
                Havre, Pamela A.
            (K) RELEVANT RESIDUES IN SEQ ID NO:1: FROM 1 TO 11

(xi) SEQUENCE DESCRIPTION: SEQ ID NO: 1:

NAGGAAGGGG G                                                                    11

(2) INFORMATION FOR SEQ ID NO: 2:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

AGGAAGGGGG                                                                      10

(2) INFORMATION FOR SEQ ID NO: 3:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

GGGGGAAGGA                                                                      10

(2) INFORMATION FOR SEQ ID NO: 4:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

CCCCCTTC                                                                         8

(2) INFORMATION FOR SEQ ID NO: 5:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: misc_feature
            (B) LOCATION: 1..11
            (D) OTHER INFORMATION: /function= "N is
                4'-hydroxymethyl-4,5',8-trimethylpsoralen"

(xi) SEQUENCE DESCRIPTION: SEQ ID NO: 5:

NGGGGGAAGG A                                                           11

(2) INFORMATION FOR SEQ ID NO: 6:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 6:

GGTTCGAATC CTTCCCCC                                                    18

(2) INFORMATION FOR SEQ ID NO: 7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 7:

GGTTCGAAAC CTTCCCCC                                                    18

(2) INFORMATION FOR SEQ ID NO: 8:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 8:

TGGTGGTGGG GGAAGGATTC GAACCTTCGA AGTCG                                  35

(2) INFORMATION FOR SEQ ID NO: 9:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 9:

CGACTTCGAA GGTTCGAATC CTTCCCCCAC CACCA                                    35

(2) INFORMATION FOR SEQ ID NO: 10:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1..60
        (D) OTHER INFORMATION: /function= "At positions 16 and 57,
            N is G or T."

(ix) FEATURE:
        (A) NAME/KEY: misc_feature
        (B) LOCATION: 1..121
        (D) OTHER INFORMATION: /function= "At position 17, N is A,
            G or T."

(ix) FEATURE:
        (A) NAME/KEY: misc_feature
        (B) LOCATION: 1..121
        (D) OTHER INFORMATION: /function= "At position 18, N is A,
            C or T."

(ix) FEATURE:
        (A) NAME/KEY: misc_feature
        (B) LOCATION: 1..121
        (D) OTHER INFORMATION: /function= "At position 20, N is G
            or A."

(ix) FEATURE:
        (A) NAME/KEY: misc_feature
        (B) LOCATION: 1..121
        (D) OTHER INFORMATION: /function= "At position 24, N is C
            or T."

(xi) SEQUENCE DESCRIPTION: SEQ ID NO: 10:

TGGTGGTGGG GGAAGNNNTN GAANCTTCGA AGTCGATGAC GGCAGATTTA GAGTCTNCTC           60

CCTTTGGCCG CTCGGGAACC CCACCACAGG TAATGCTTTT ACGGGGCGCA TCATATCAA          120

T                                                                        121

(2) INFORMATION FOR SEQ ID NO: 11:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 11:

-continued

```
ATTTGATATG ATGCGCCCCG TAAAAGCATT ACCTGTGGTG GGGTTCCCGA GCGGCCAAAG    60

GGAGCAGACT CTAAATCTGC CGTCATCGAC TTCGAAGGTT CGAATCCTTC CCCCACCAC    120

A                                                                    121
```

(2) INFORMATION FOR SEQ ID NO: 12:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1..121
        (D) OTHER INFORMATION: /function= "At position 7, N is G
            or T."

(ix) FEATURE:
        (A) NAME/KEY: misc_feature
        (B) LOCATION: 1..121
        (D) OTHER INFORMATION: /function= "At positions 12, 20 and
            117, N is C or G."

(ix) FEATURE:
        (A) NAME/KEY: misc_feature
        (B) LOCATION: 1..121
        (D) OTHER INFORMATION: /function= "At positions 15, 16,
            21, 29, 78, 83 and 108, N is A or G."

(ix) FEATURE:
        (A) NAME/KEY: misc_feature
        (B) LOCATION: 1..121
        (D) OTHER INFORMATION: /function= "At positions 18, 49,
            68, 69, and 107, N is C or T."

(ix) FEATURE:
        (A) NAME/KEY: misc_feature
        (B) LOCATION: 1..121
        (D) OTHER INFORMATION: /function= "At position 114, N is
            C, T or A."

(xi) SEQUENCE DESCRIPTION: SEQ ID NO: 12:

```
TGGTGGNGGG GNAANNANTN NAACCTTCNA AGTCGATGAC GGCAGATTNN GAGTCTNCTC    60

CCTTTGGNNG CTCGGGANCC CCNCCACAGG TAATGCTTTT ACGGGGNNCA TCANNTNAA    120

T                                                                    121
```

(2) INFORMATION FOR SEQ ID NO: 13:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1..121
        (D) OTHER INFORMATION: /function= "At position 16, N is G
            or A."

```
    (ix) FEATURE:
        (A) NAME/KEY: misc_feature
        (B) LOCATION: 1..121
        (D) OTHER INFORMATION: /function= "At position 17, N is A
             or T."

(ix) FEATURE:
        (A) NAME/KEY: misc_feature
        (B) LOCATION: 1..121
        (D) OTHER INFORMATION: /function= "At position 19, N is T
             or C."

(xi) SEQUENCE DESCRIPTION: SEQ ID NO: 13:

TGGTGGTGGG GGAAGNNTNC GAACCTTCGA AGTCGATGAC GGCAGATTTA GAGTCTNCTC      60

CCTTTGGCCG CTCGGGAACC CCACCACAGG TAATGCTTTT ACGGGGCGCA TCATATCAA     120

T                                                                    121
```

CHEMICALLY MODIFIED OLIGONUCLEOTIDE FOR SITE-DIRECTED MUTAGENESIS

This application is a continuation of U.S. Ser. No. 08/083,088 filed Jun. 25, 1993 now abandoned.

BACKGROUND OF THE INVENTION

This relates to the fields of genetics, and more particularly relates to site-directed mutagenesis of a gene of interest.

Gene Therapy

Gene therapy is the introduction into a cell of an entire replacement copy of a defective gene to treat human, animal and plant genetic disorders. The introduced gene, via genetic recombination, replaces the endogenous gene. This approach requires complex delivery systems to introduce the replacement gene into the cell, such as genetically engineered viruses, or viral vectors.

Gene therapy is being used on an experimental basis to treat well known genetic disorders of humans such as retinoblastoma and cystic fibrosis. However, in vivo efficiency is low due to the limited number of recombination events actually resulting in replacement of the defective gene.

Triple-Stranded DNA

Since the initial observation of triple-stranded DNA many years ago by Felsenfeld et al., *J. Am. Chem. Soc.* 79:2023 (1957), oligonucleotide-directed triple helix formation has emerged as a valuable tool in molecular biology. Current knowledge suggests that oligonucleotides can bind as third strands of DNA in a sequence specific manner in the major groove in homopurine/homopyrimidine stretches in duplex DNA. In one motif, a homopyrimidine oligonucleotide binds in a direction parallel to the purine strand in the duplex, as described by Moser and Dervan, *Science* 238:645 (1987), Praseuth et al., *Proc. Natl. Acad. Sci. USA* 85:1349 (1988), and Mergny et al., *Biochemistry* 30:9791 (1991). In the alternate purine motif, a homopurine strand binds antiparallel to the purine strand, as described by Beal and Dervan, *Science* 251:1360 (1991). The specificity of triplex formation arises from base triplets (AAT and GGC in the purine motif) formed by hydrogen bonding; mismatches destabilize the triple helix, as described by Mergny et al., *Biochemistry* 30:9791 (1991) and Beal and Dervan, *Nuc. Acids Res.* 11:2773 (1992).

Triplex forming oligonucleotides have been found useful for several molecular biology techniques. For example, triplex forming oligonucleotides designed to bind to sites in gene promoters have been used to block DNA binding proteins and to block transcription both in vitro and in vivo. (Maher et al., *Science* 245:725 (1989), Orson et al., *Nucleic Acids Res.* 19:3435 (1991), Postal et al., *Proc. Natl. Acad. Sci. USA* 88:8227 (1991), Cooney et al., *Science* 241:456 (1988), Young et al., *Proc. Natl. Acad. Sci. USA* 88:10023 (1991), Maher et al., *Biochemistry* 31:70 (1992), Duval-Valentin et al., *Proc. Natl. Acad. Sci. USA* 89:504 (1992), Blume et al., *Nucleic Acids Res.* 20:1777 (1992), Durland et al., *Biochemistry* 30:9246 (1991), Grigoriev et al., *J. of Biological Chem.* 267:3389 (1992), and Takasugi et al., *Proc. Natl. Acad. Sci. USA* 88:5602 (1991)). Site specific cleavage of DNA has been achieved by using triplex forming oligonucleotides linked to reactive moieties such as EDTA-Fe(II) or by using triplex forming oligonucleotides in conjunction with DNA modifying enzymes (Perrouault et al., *Nature* 344:358 (1990), Francois et al., *Proc. Natl. Acad. Sci. USA* 86:9702 (1989), Lin et al., *Biochemistry* 28:1054 (1989), Pei et al., *Proc. Natl. Acad. Sci. USA* 87:9858 (1990), Strobel et al., *Science* 254:1639 (1991), and Posvic and Dervan, *J. Am. Chem Soc.* 112:9428 (1992)). Sequence specific DNA purification using triplex affinity capture has also been demonstrated. (Ito et al., *Proc. Natl. Acad. Sci. USA* 89:495 (1992)). Triplex forming oligonucleotides linked to intercalating agents such as acridine, or to cross-linking agents, such as p-azidophenacyl and psoralen, have been utilized, but only to enhance the stability of triplex binding. (Praseuth et al., *Proc. Natl. Acad. Sci. USA* 85:1349 (1988), Grigoriev et al., *J. of Biological Chem.* 267:3389 (1992), Takasugi et al., *Proc. Natl. Acad. Sci. USA* 88:5602 (1991).

A method for site-directed mutagenesis of a target DNA molecule would be a useful in achieving successful gene or anti-viral therapy. Such a method would also be a useful research tool for genetic engineering or for studying genetic mechanisms such as DNA repair.

Therefore, it is an object of the present invention to provide a method for in vivo and in vitro site-directed mutagenesis of a target DNA molecule.

It is a further object of the present invention to provide a method for mutagenesis of a target DNA molecule that is highly specific and efficient.

It is a further object of the present invention to provide a method for treating genetic disorders by gene therapy without the need for a viral vector.

It is a further object of the present invention to provide a method for treating cancer.

It is a further object of the present invention to provide a mutagenic oligonucleotide for use in therapy and research.

SUMMARY OF THE INVENTION

A mutagenic, triplex-forming oligonucleotide and methods for use thereof are described herein. An oligonucleotide capable of forming a triple strand with a specific DNA segment of a target gene DNA is chemically modified to incorporate a mutagen. The modified oligonucleotide hybridizes to a chosen site in the target gene, forming a triplex region, thereby bringing the attached mutagen into proximity with the target gene and causing a mutation at a specific site in the gene. The mutation activates, inactivates or alters the activity and function of the target gene.

If the target gene contains a mutation that is the cause of a genetic disorder, then the mutagenic oligonucleotide is useful for mutagenic repair that may restore the DNA sequence of the target gene to normal. If the target gene is a viral gene needed for viral survival or reproduction or an oncogene causing unregulated proliferation, such as in a cancer cell, then the mutagenic oligonucleotide is useful for causing a mutation that inactivates the gene to incapacitate or prevent reproduction of the virus or to terminate or reduce the uncontrolled proliferation of the cancer cell. The mutagenic oligonucleotide is also a useful anti-cancer agent for activating a repressor gene that has lost its ability to repress proliferation.

The mutagenic triplex-forming oligonucleotide can also be used as a molecular biology research tool to cause site-directed or targeted mutagenesis. Site-directed mutagenesis is useful for targeting a normal gene and for the study of mechanisms such as DNA repair. Targeted mutagenesis of a specific gene in an animal oocyte, such as a mouse oocyte, provides a useful and powerful tool for genetic engineering for research and therapy and for generation of new strains of "transmutated" animals and plants for research and agriculture.

BRIEF DESCRIPTION OF THE DRAWINGS

FIGS. 2A and 2B show a sequence analysis of targeted mutagenesis in the supF gene by the psoralen-linked triplex-forming oligonucleotide (pso-AG10). In FIG. 2A, mutations produced by pso-AG10 and UVA are indicated above each base pair, with the listed base representing the change from the sequence in the top strand. The + signs below the sequence are sites at which mutations are known to produce a detectable phenotype change, demonstrating that the use of supF in this assay does not bias detection at any particular site. The asterisk indicates the targeted base pair at position 167. DNA sequence data was obtained by automated methods after polymerase chain reaction amplification of the supF genes from lambda phage plaques in accordance with the method of Connell et al., *Biotechniques* 5:342 (1987). FIG. 2B is a compilation of mutations induced in supF by 8-methoxypsoralen and UVA in mouse L-cells using the lambda supF vector of FIG. 1 or generated using a plasmid shuttle vector in monkey Vero cells in accordance with the method of Bredberg and Nachmansson, *Carcinogenesis* 8:1923 (1987), to compare the mutations produced in supF by free psoralen with those produced by the triplex forming oligonucleotide AG10.

FIG. 4 is a schematic representation showing the basis of a restriction enzyme protection assay to detect site-specific triplex formation within the supF gene. The formation of triplex DNA by psoralen-AG10 at its targeted site (bp 167–176 of the supF gene) overlaps with the Hinf I restriction site at bp 164–168 (indicated in the diagram by the box around the appropriate base pairs). Digestion of the unprotected 250 bp supF PCR fragment with Hinf I is expected to yield three fragments of sizes 150, 65, and 35 bp. In contrast, with the Hinf I site at bp 164–168 blocked by triplex formation at bp 167–176, fragments of sizes 150 and 100 bp are predicted.

FIGS. 5A and 5B are a sequence analysis of targeted mutagenesis in the supF gene within the pSP189 SV40 vector by the psoralen-linked triplex-forming oligonucleotide, psoralen-AG10. In FIG. 5A, point mutations produced by psoralen-AG10 and UVA are indicated above each base pair, with the listed base representing the change from the sequence in the top strand. Deletion mutations are presented below the supF sequence, indicated by dashed lines. For the one deletion that was accompanied by an apparent base change, the indicated base represents a mutation from the sequence of the top strand. The + signs below the sequence are sites at which mutations are known to produce a detectable phenotype change demonstrating that the use of supF in this assay does not bias detection at any particular site. The asterisk indicates the targeted base pair at position 167. FIG. 5B is a compilation of mutations induced in supF by 8-methoxypsoralen and UVA in mouse L-cells using a lambda phage shuttle vector or generated in monkey Vero cells using an SV40 shuttle vector (pZ189) almost identical to the one used in this study to show for comparison the mutations that can be produced in supF by free psoralen.

DETAILED DESCRIPTION OF THE INVENTION

Figure 1:
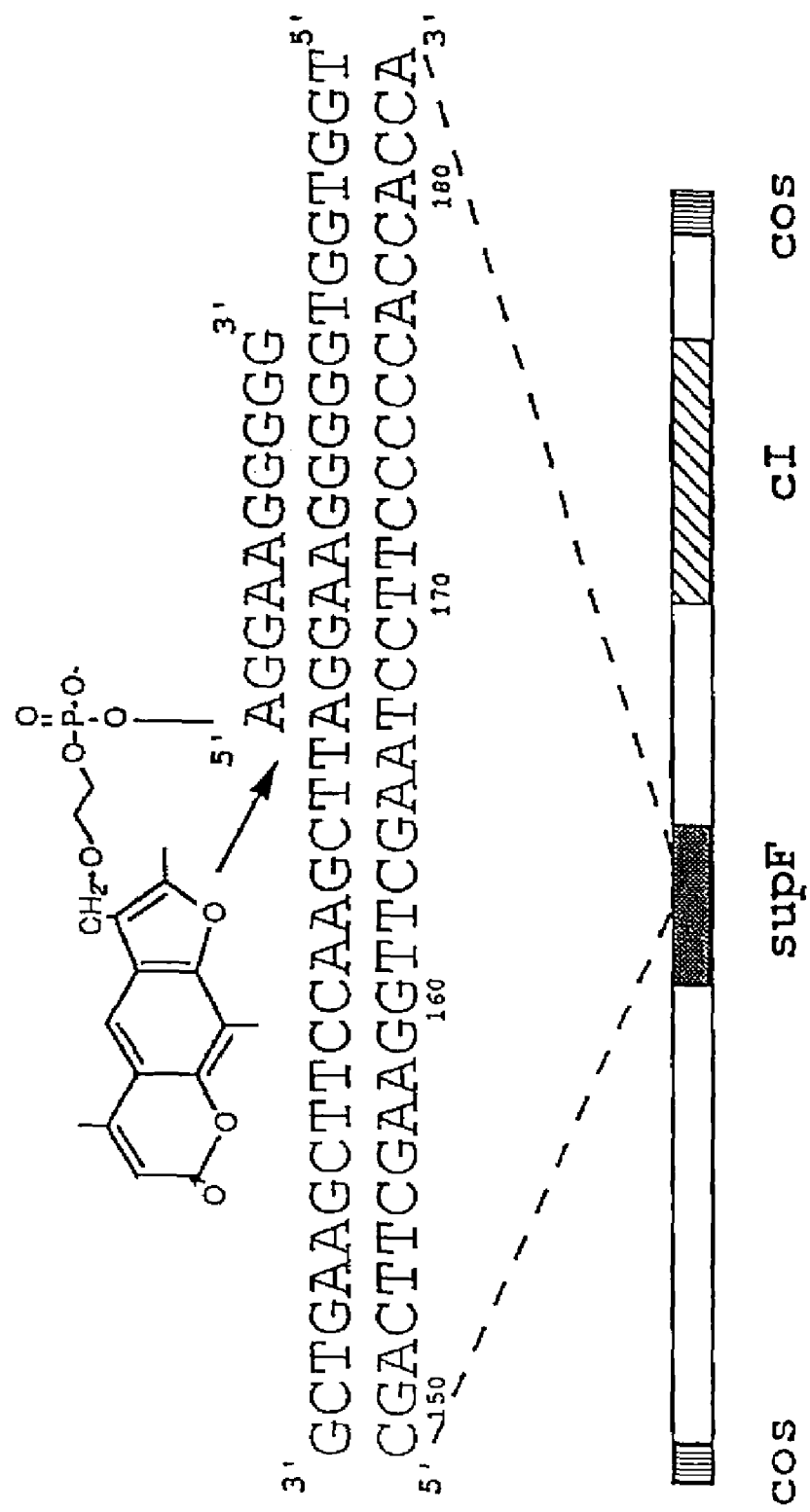
FIG. 1 is a schematic representation showing a psoralen-linked triplex-forming oligonucleotide for targeted mutagenesis of the lambda genome. A map of the lambda supF genome is shown, including the target gene for site-directed mutagenesis, the supF suppressor tRNA gene. Above the partial sequence of the supF gene (positions 149 to 183), the site of triplex formation at positions 167–176 is indicated by the placement of the triplex-forming oligonucleotide, pso-AG10 (4'-hydroxymethyl-4,5',8-trimethylpsoralen-5'AGGAAGGGGG3') (SEQ ID NO:1). The arrow indicates that the psoralen moiety is targeted to the A:T base pair at position 167. In addition to the supF gene, the lambda vector carries the cI lambda repressor gene which is used to assess non-targeted mutagenesis.

A mutagenic triplex-forming oligonucleotide and methods of use in gene therapy, anti-viral therapeutics, molecular biology research, and genetic engineering of cells, animals and plants are provided. The mutagenic oligonucleotide binds with specificity to a chosen site in a target DNA molecule, forming a triplex region, thereby bringing the attached mutagen into proximity with the target site and causing a mutation therein. Preferably, the mutation activates, inactivates or alters the activity and function of a gene containing the target site.

Oligonucleotide

The oligonucleotide is a synthetic or isolated oligonucleotide capable of binding or hybridizing with specificity to a predetermined region of a double-stranded DNA molecule to form a triple-stranded structure. Preferably the predetermined region of the double-stranded molecule contains or is adjacent to the defective or essential portion of a target gene, such as the site of a mutation causing a genetic defect, a site causing oncogene activation, or a site causing the inhibition or inactivation of an oncogene suppressor. Most preferably, the gene is a human gene.

Preferably the oligonucleotide is a single-stranded DNA molecule between 7 and 30, most preferably 10 to 20, nucleotides in length. The base composition is preferably homopurine or homopyrimidine. However, other compositions are also useful. The preferred conditions under which a triple-stranded structure will form are well known to those skilled in the art.

Mutagen

The oligonucleotide is chemically modified to include a mutagen at either the 5' end, 3' end, or internal portion so that the mutagen is proximal to the site in the gene requiring modification. Preferably the mutagen is incorporated into the oligonucleotide during nucleotide synthesis. For example, commercially available compounds such as psoralen C2 phosphoramidite (Glen Research, Sterling, Va.) are inserted into a specific location within an oligonucleotide sequence in accordance with the methods of Takasugi et al., *Proc. Natl. Acad. Sci. U.S.A.* 88:5602–5606 (1991), Gia et al., *Biochemistry* 31:11818–11822 (1992), Giovannangeli et al., *Nucleic Acids Res.* 20:4275–4281 (1992) and Giovannangeli et al., *Proc. Natl. Acad. Sci. U.S.A.* 89:8631–8635 (1992), all of which are incorporated by reference herein.

The mutagen may also be attached to the oligonucleotide by a covalent bond. For example, the mutagen is attached to the oligonucleotide by a linker, such as sulfo-m-maleimidobenzoly-N-hydroxysuccinimide ester (sulfo-MBS, Pierce Chemical Co., Rockford, Ill.) in accordance with the methods of Liu et al., *Biochem.* 18:690–697 (1979) and Kitagawa and Ailawa, *J. Biochem.* 79:233–236 (1976), both of which are incorporated by reference herein. Alternatively, the mutagen is attached to the oligonucleotide by photoactivation, which causes the mutagen, such as psoralen, to bind to the oligonucleotide.

The mutagen can be any chemical capable of causing a mutation at the desired site of the double-stranded DNA molecule. Preferably the mutation restores the normal, functional sequence of the gene, inactivates an oncogene or activates an oncogene suppressor, or alters the function or inactivates a viral gene.

The chemical mutagen can either cause the mutation spontaneously or subsequent to activation of the mutagen, such as, for example, by exposure to light.

Preferred mutagens include psoralen, which requires activation by UVA irradiation, acridine orange, which can be activated by UVA irradiation and can be activated in the absence of light, and alkylating agents, cis-platinum analogs, hematoporphyrins and hematoporphyrin derivatives, mitomycin C, radionuclides such as $^{125}$I, $^{35}$S and $^{32}$P, and molecules that interact with radiation to become mutagenic, such as boron that interacts with neutron capture and iodine that interacts with auger electrons. In particular, acridine orange can be used to cause a frame shift mutation, useful for gene inactivation.

If necessary for activation of the mutagen, light can be delivered to cells on the surface of the body, such as skin cells, by exposure of the area requiring treatment to a conventional light source. Light can be delivered to cells within the body by fiber optics or laser by methods known to those skilled in the art. Targeted fluorogens that provide sufficient light to activate the light-activated mutagens can also provide a useful light source.

Method of Administration

Preferably, the mutagenic oligonucleotides are dissolved in a physiologically-acceptable carrier, such as an aqueous solution or are incorporated within liposomes, and the carrier or liposomes are injected into the organism undergoing genetic manipulation, such as an animal requiring gene therapy or anti-viral therapeutics. The preferred route of injection in mammals is intravenous. It will be understood by those skilled in the art that oligonucleotides are taken up by cells and tissues in animals such as mice without special delivery methods, vehicles or solutions.

For in vitro research studies, a solution containing the mutagenic oligonucleotides is added directly to a solution containing the DNA molecules of interest in accordance with methods well known to those skilled in the art and described in more detail in the examples below.

Methods of Use

If the target gene contains a mutation that is the cause of a genetic disorder, then the mutagenic oligonucleotide is useful for mutagenic repair that may restore the DNA sequence of the target gene to normal. If the target gene is an oncogene causing unregulated proliferation, such as in a cancer cell, then the mutagenic oligonucleotide is useful for causing a mutation that inactivates the gene and terminates or reduces the uncontrolled proliferation of the cell. The mutagenic oligonucleotide is also a useful anti-cancer agent for activating a repressor gene that has lost its ability to repress proliferation. Furthermore, the mutagenic oligonucleotide is useful as an antiviral agent when the oligonucleotide is specific for a portion of a viral genome necessary for proper proliferation or function of the virus.

The mutagenic triplex-forming oligonucleotide can also be used as a molecular biology research tool to cause site-directed mutagenesis in any gene for the study of mechanisms such as, for example, DNA repair. The oligonucleotide may also be used to study DNA repair by delivering an adduct to the DNA and studying how the adduct is processed into a mutation under various experimental conditions.

The mutagenic triplex-forming oligonucleotides will be further understood in view of the following non-limiting examples.

EXAMPLE 1

Site-Specific, Targeted Mutagenesis of the SupF Gene of the Lambda Phage Genome

A triplex-forming oligonucleotide linked to psoralen at its 5' end was used to achieve site-specific, targeted mutagenesis in a specific gene in an intact, double-stranded lambda phage genome. Psoralen-linked oligonucleotides were obtained from either Oligos Etc. (Wilsonville, Oreg.) or M. Talmor (Yale University, New Haven, Conn.) with materials from Glen Research (Sterling, Va.). The psoralen was incorporated in the oligonucleotide synthesis as a psoralen phosphoramidite in accordance with the instructions provided by supplier.

Site-specific triplex formation was designed to deliver the psoralen to the targeted site in the lambda DNA, and UVA irradiation was used to activate the psoralen to form adducts and thereby induce mutations at that site. Sequence analysis of mutations in the target gene showed that almost all were in the targeted region, and 56% were found to be the same T:A to A:T transversion at the targeted base pair. The ratio of targeted to non-targeted mutagenesis was estimated by simultaneous analysis of mutagenesis in a non-targeted gene within the lambda genome, along with analysis of mutagenesis induced by a non-triplex forming (but psoralen linked) oligonucleotide. It was found that targeted mutations were produced at a frequency at least 500-fold greater than that of non-targeted mutations.

The target gene chosen was supF, an *E. coli* amber suppressor tyrosine tRNA gene, contained within the genome of a lambda phage vector, lambda supF as shown in FIG. 1. A 10 base homopurine oligonucleotide AG10 (5'AG-GAAGGGGG 3') capable of forming a triple strand at positions 167–176 in the supF gene was identified. The ability of AG10 to bind to the supF gene was demonstrated using $^{32}$P-labeled AG10 in an in vitro binding reaction with a 250 bp fragment containing the entire supF gene.

To demonstrate targeted, site-specific triplex formation as a prelude to mutagenesis studies, binding assays were carried out for 2 hours at 37 degrees in 10% sucrose, 20 mM $MgCl_2$, 10 mM Tris (pH 8.0), and 1 mM spermidine in a 10 µl volume. The 250 bp supF target was generated from lambda supF using the polymerase chain reaction. Each oligo (200 ng) was labelled with 50 µCi of gamma-$^{32}$P-ATP (Amersham, Arlington Heights, Ill.) and separated from unreacted gamma$^{32}$P-ATP by passage through a G-25 spin column (Boehringer Mannheim, Indianapolis, Ind.). The concentration of oligomer in the reaction mixture was $6 \times 10^{-8}$ M and the oligomer:supF ratio was approximately 1:1 on a molar basis. When present, competitors were used at 200-fold molar excess.

Following the 2 hour binding step, reaction mixtures were run on a 4% acrylamide gel in 90 mM Tris base, 90 mM boric acid, 20 mM $MgCl_2$ with a 20% acrylamide plug. A 100 bp ladder (BRL, Bethesda, Md.) was end-labelled as described for oligomers and run on gels as a size reference. Following a 4 hour run at constant voltage (150 V), the gel was visualized by autoradiography for 1 hour using Kodak X-AR film. The electrophoretic gel showed binding of the triplex forming oligonucleotide "AG10" to the supF gene target. To assay for triplex formation, $^{32}$P-labeled oligonucleotides, either AG10 ($^5$ AGGAAGGGGG$^3$) (SEQ ID NO:2) or the reverse sequence oligomer (GA10), were incubated with a 240 bp double-stranded fragment containing the entire supF gene. The products of the binding reactions were visualized by polyacrylamide gel electrophoresis and autoradiography.

Binding of labelled AG10 to the added supF DNA was demonstrated by the new band migrating at the position appropriate to the 250 bp supF fragment. When no supF target DNA was present, there was no band observed at this position. Excess unlabelled AG10 competed with the $^{32}$P-labelled AG10 whereas an excess of the reverse sequence oligomer (GA10, 5' GGGGGAAGGA 3') (SEQ ID NO:3) did not compete with AG10. In lanes 5–8, no binding of the $^{32}$P-labelled GA10 to supF was detected: GA10 alone without supF; GA10 plus supF; GA10 plus supF with excess unlabelled GA10; GA10 plus supF with excess AG10.

The reverse sequence oligomer, GA10, failed to bind to supF or to compete with AG10 for binding. AG10 linked to 4'hydroxymethyl-4,5',8-trimethylpsoralen via a 2 carbon linker arm (pso-AG10) formed a covalent bond to labeled duplex supF DNA following UVA irradiation, whereas the reverse oligomer (pso-GA10) did not.

Targeted mutagenesis was achieved by incubating pso-AG10 with lambda supF DNA in vitro to form triplex at positions 167 to 176 of the supF gene and bring the tethered psoralen into proximity with the targeted base pair at position 167 as shown in Table 1. The numbers in the table represent the frequency of mutations seen in either the supF gene or the cI gene in the lambda supF genome following the indicated treatment. The lambda DNA at 3 nM was incubated with or without a 1000-fold molar excess of the indicated oligonucleotides (3 µM) as described in FIG. 2.

UVA (365 nm) irradiation of selected samples was performed at a dose of 1.8 $J/cm^2$. A radiometer was used to measure lamp output (typical UVA irradiance of 5–7 $mW/cm^2$ at 320–400 nm). The DNA was packaged in vitro into phage particles, using the method of Hohn, *Methods in Enzymology* 68:299–309 (1979), and the phage particles were adsorbed to *E. coli* and grown as individual plaques to allow genetic analyses of the supF and cI genes. AG10 bound specifically to the supF gene, whereas the reverse sequence GA10 did not bind.

CT8 (row 3), complementary to the 3' eight nucleotides of AG10, was preincubated with psoralen-AG10 for 30 min at a 1:1 ratio to form duplex DNA and partially inhibit the ability to psoralen-AG10 to form triplex at the targeted site in the supF gene.

Photoactivation of the psoralen generated a DNA adduct, and in vitro packaging of the psoralen-AG10. The lambda supF DNA complex allowed growth of the phage in bacteria to fix the adduct into a mutation. The phage particles were grown as individual plaques on a bacterial lawn to detect targeted mutagenesis in the supF gene and to measure the extent of non-targeted mutagenesis by screening for the function of an unrelated gene, the lambda repressor (cI) gene. Mutations in these genes yield colorless plaques among blue ones and clear plaques among turbid ones, respectively.

Pso-AG10 plus UVA treatment of the lambda DNA resulted in a mutation frequency of 0.233% in supF but approximately 100-fold less, 0.0024%, in cI. The specificity of the targeted mutagenesis is most likely even greater than this 100-fold difference, perhaps as much as 500-fold, considering that cI (765 bp) is a bigger target for mutagenesis than supF (184 bp) and the percentage of base pairs in the two genes at which mutations are detectable was similar. This difference in target size was demonstrated by the 5-fold difference in supF versus cI mutants induced by the reverse oligomer, pso-GA10. In addition, the reverse oligomer gave a 582-fold lower frequency of supF mutations (0.0004%) than did pso-AG10, but yielded a similar frequency of cI mutations. In fact, mutagenesis by the reverse oligomer was barely above background (untreated lambda DNA).

To partially inhibit formation of the triplex, an 8 base oligomer (CT8) complementary to 8 of the 10 bases of AG10 (5' CCCCCTTC 3') (SEQ ID NO:4) was preincubated at a 1:1 ratio with pso-AG10 to form a double-stranded complex. When this pre-formed complex was incubated with lambda supF and irradiated with UVA, it yielded only 0.016% supF mutations, 15-fold less than with psoralen-AG10 alone. No significant mutagenesis was produced by UVA alone (1.8 $J/cm^2$) in the absence of the pso-AG10 or by pso-AG10 without UVA, demonstrating the importance of activation of the psoralen by UVA and showing that triplex formation, by itself, was not mutagenic. This data provided genetic evidence for the targeted mutagenesis of the supF gene by pso-AG10.

TABLE 1

Targeted mutagenesis of the supF gene in lambda supF DNA produced by a psoralen-linked triplex-forming oligonucleotide (pso-AG10) plus UVA irradiation.

| Treatment of lambda DNA | Sequence of oligonucleotide(s) | supF mutations per 1000 phage | cI mutations per 1000 phage |
|---|---|---|---|
| pso-AG10 | pso-5'AGGAAGGGGG3' (SEQ ID NO:1) | 2.33 (263/112.872) | 0.024 (28/1,162,000) |
| pso-GA10 | pso-5'GGGGGAAGGA3' (SEQ ID NO:5) | 0.004 (2/504.198) | 0.019 (9/483,475) |
| pso-AG10 plus CT8 | pso-5'AGGAAGGGGG3' (SEQ ID NO:1) and (SEQ ID NO:4) 3'CTTCCCCC5' (SEQ ID NO:1) and (SEQ ID NO:4) | 0.16 (12/72,625) | 0.014 (8/557,136) |
| UVA alone | n.a. | <0.018 (0/55,000) | n.t. |
| pso-AG10 alone no UVA | pso-5'AGGAAGGGGG3' (SEQ ID NO:1) | <0.014 (0/69.000) | n.t. |
| None | n.a. | <0.003 (0/328,500) | 0.009 (10/1,150,000) |

EXAMPLE 2

Sequence Analysis of Mutants Obtained by Targeted Mutagenesis Using the Triplex-Forming Oligonucleotide To obtain direct evidence for targeted mutagenesis, a series of independent mutants produced in the supF gene of the lambda vector by pso-AG10 and UVA were sequenced. The sequences of 25 such mutants are presented in FIG. 2a. All except one of the 25 mutations produced by pso-AG10 is at or near the targeted T:A base pair at position 167. 56% of the mutations consist of the same T:A to A:T transversion precisely at the targeted base pair (#167), demonstrating the specificity and reproducibility of the targeting by pso-AG10. The A:T base pair at 167 forms a triplet with the 5' adenine to which the psoralen is tethered in AG10, and so it is the closest base pair to the psoralen. The overwhelming predominance of the T:A to A:T transversion at this site is consistent with the mutagenic action of psoralen, which tends to form adducts at pyrimidines, and especially at thymidines. It should be noted that these mutations are independent and none of the mutations represent siblings because each packaged lambda particle gives rise to a single, separate lambda plaque on the bacterial lawn.

Figures 2A, 2B:
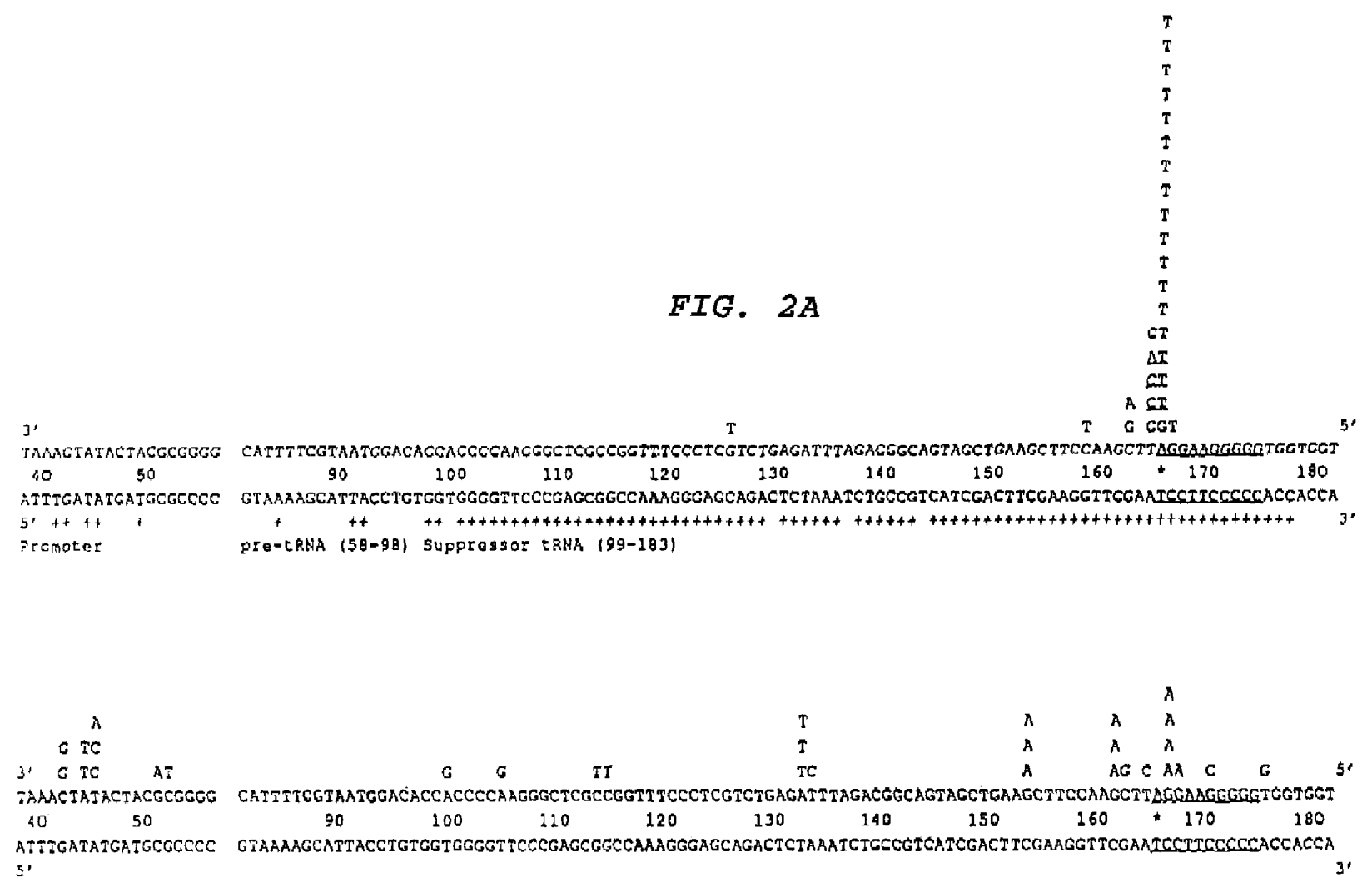

Mutations found to be induced in the supF gene by free 8-methoxypsoralen and UVA in other experimental systems employing shuttle vectors, as described by Glazer et al., *Proc. Natl. Acad. Sci. USA* 83:1041 (1986) and Bredberg and Nachmansson, *Carcinogenesis* 8:1923 (1987), which are incorporated by reference herein, are shown in FIG. 2b. This compiled data demonstrates that free psoralen can form adducts and induce mutations at many different sites in supF apart from base pair 167. The scattered distribution of mutations is in contrast with the specific mutagenesis induced by the triplex-forming pso-AG10. Although several of the mutations listed in FIG. 2b fall in the region of the homopurine/homopyrimidine run at positions 167 to 176, none of them occur at position 167. Neither of the two mutations induced by the reverse oligomer, pso-GA10, were found to occur at base pair 167.

The spectrum of the mutations produced by pso-AG10 indicates that almost all were targeted by the triplex-forming oligonucleotide. Although a majority of the mutations were at the targeted position 167 and consisted of the same T:A to A:T transversion, several mutations were at base pairs nearby to position 167. It is possible that the psoralen moiety, tethered to AG10 on a 2 carbon linker arm, may occasionally reach beyond the T:A base pair at 167 to form adducts at nearby pyrimidines, giving rise to mutations. It is also possible that even if an adduct is formed at position 167, the bacterial polymerase and repair enzymes that fix the adduct into a mutation may generate mutations at nearby sites during repair and replication while at the same time repairing or bypassing the adduct at 167. The occurrence of several mutations that involve base changes at two adjacent base pairs (166 and 167 in all 3 instances) supports the notion that an adduct at position 167 can cause a change at a nearby position. The rare non-specific mutagenesis by pso-AG10 (and the very small amount of mutagenesis by-pso-GA10 that is above background) may result from the potential ability of the psoralen molecule, in spite of being tethered to the oligonucleotide, to intercalate into and form adducts at random sites in the DNA. A reduction of this non-specific activity may be achieved by reducing the reach and the degrees of freedom of the psoralen by attaching it to the triplex-forming oligonucleotide by a shorter tether, such as a one carbon linker arm, or by direct linkage of the psoralen to the nucleotide in the triplex-forming oligonucleotide by direct photoactivation of free psoralen to bind to the oligonucleotide, and the purification of the desired product.

This experiment achieved a targeted mutation frequency of 0.233%.

EXAMPLE 3

Covalent Linkage of Psoralen to an Oligonucleotide

The mutagen, 5-aminomethyl-8-methoxypsoralen, was covalently linked to an oligonucleotide.

5-aminomethyl-8-methoxypsoralen (5am8mop, HRI Associates, Emeryville, Calif.) was mixed with the linker, sulfo-m-maleimidobenzoyl-N-hydroxysuccinimide ester (sulfo-MBS, Pierce Chemical Co., Rockville, Ill.) in 0.05 M phosphate buffer, pH 8, with a 5am8mop to sulfo-MBS molar ratio of 1:40. The mixture was stirred at room temperature for 30 minutes while protected from light in accordance with the methods of Liu et al., *Biochem.* 18:690–697 (1979) and Kitagawa and Ailawa, *J. Biochem.* 79:233–236 (1976), and the instructions of the Pierce Immunotechnology Catalog and Handbook, 1992–93 edition, pages A16–A17. The initial run was made using 1 ml total volume and 1 mM 5am8mop, with the reaction scaled up and optimized as needed.

The modified 5am8mop was purified by HPLC using a modification of standard conditions used in the analysis of 8-methoxypsoralen as described by Gasparro et al., *J. Invest. Derm.* 90:234–236 (1988). The initial conditions were: a Regis Rexchrom™ phenyl 15 cm HPLC column running a gradient between acetonitrile and either water or 0.05 M, pH 4.5 ammonium acetate buffer. A linear gradient was run from 10% acetonitrile to 60% acetonitrile over 50 minutes. When buffer was needed in the initial purification run, the sample was collected off the HPLC, evaporated, and desalted by passing it through the HPLC again with an acetonitrile:water gradient mixture. The detector was a SpectraFocus™ scanning UV detector with wavelengths from 220 to 360 sampled. The detector was connected to a Pharmacia Frac-100™ fraction collector.

The purified, modified 5am8mop was then reacted with an oligonucleotide containing an —SH tether by mixing equimolar amounts of modified 5am8mop with the oligonucleotide in 0.05 M phosphate buffer, pH 7–7.5 at room temperature for three hours while protected from light.

The oligonucleotide tethered to 5am8mop was then purified by HPLC using a modification of the method of Gasparro et al., *Antisense Res. Dev.* 1:117–140 (1991). A Nest Group MRPH 10 cm HPLC column running a linear gradient of 5% to 20% acetonitrile over 40 minutes between acetonitrile and 0.2 M pH 5.9 triethylammonium acetate buffer was used.

EXAMPLE 4

Targeted Mutagenesis of SV40 DNA Using Triple Helix-Forming Oligonucleotides The following was performed to investigate targeted mutagenesis of SV40 DNA transfected into monkey cells. In these experiments, the site-specific triplex formation was designed to deliver the psoralen to the targeted site in the SV40 DNA, UVA irradiation was used to activate the psoralen to form adducts at that site, and repair and replication of the viral genomes in the monkey cells fix the adducts into mutations. These results demonstrate that targeted mutagenesis occurs even more efficiently in mammalian cells (6% of SV40 genomes incurred targeted mutations) than in bacteria (0.2%).

Materials and Methods

Figure 3:
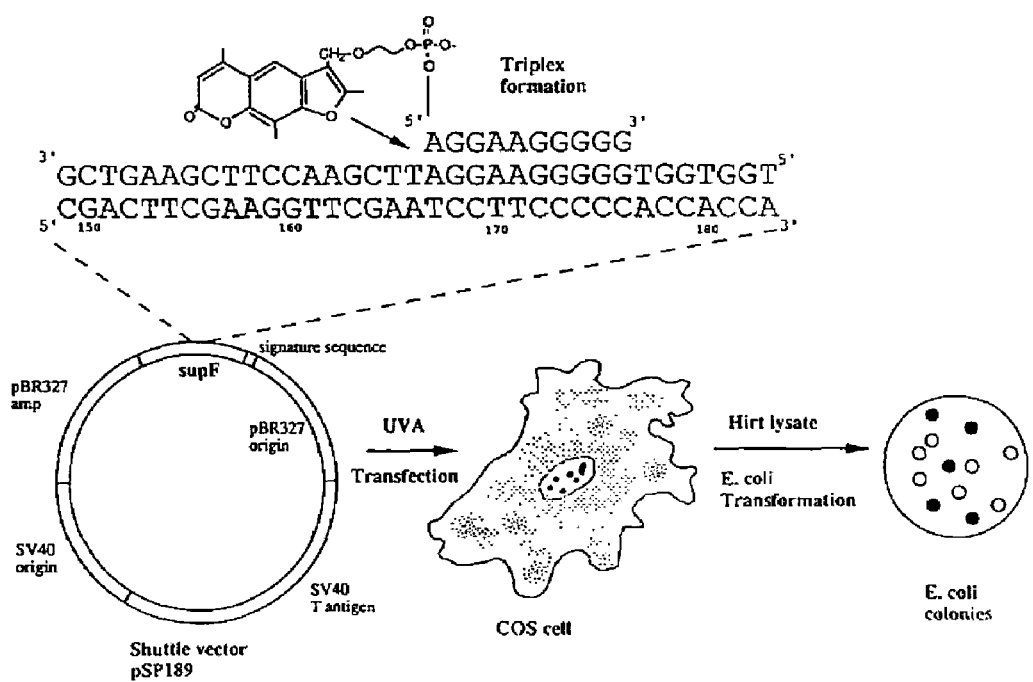
FIG. 3 is a schematic representation of the strategy for targeted mutagenesis of SV40 DNA. The 10 base triplex-forming oligonucleotide, psoralen-AG10 (4'hydroxymethyl-4,5',8-trimethylpsoralen-5'AGGAAGGGGG3') (SEQ ID NO:1), is shown directly above its targeted sequence in the supF gene (base pairs 167–176), contained within the SV40 vector, pSP189. Psoralen-AG10 is incubated with the SV40 vector DNA to allow site-specific triplex formation. Photoactivation of the psoralen by irradiation with long wave ultraviolet light (320–400 nm) is designed to generate an adduct at the targeted base pair (167), as indicated by the arrow. The oligo-plasmid complex is then transfected into monkey COS-7 cells and allowed to replicate for 48 hours. Following purification of the vector DNA by the Hirt lysate procedure (Hirt et al., *J. Mol. Biol.* 26:365–369 (1967)), the DNA is used to transform *E. coli* SY204 lacZ125 (Am). Transformants are selected on ampicillin plates containing X-gal and IPTG for detection and isolation of mutants (white colonies) in which the supF gene has been inactivated by mutation.

Oligonucleotides and vectors. Psoralen-linked oligonucleotides were obtained from either Oligos Etc. (Wilsonville, Oreg.) or M. Talmor (Yale University, New Haven, Conn.) with materials from Glen Research (Sterling, Va.). The psoralen is incorporated in the oligonucleotide synthesis as a psoralen phosphoramidite, resulting in an oligonucleotide linked at its 5' end via a two carbon linker arm to 4'-hydroxymethyl-4,5',8-trimethylpsoralen, as illustrated in FIG. 3. The sequences of oligonucleotides used in this study include AG10 (5'AGGAAGGGGG3') (SEQ ID NO:2), and GA10 (5'GGGGGAAGGA3') (SEQ ID NO:3). SV40 shuttle vector pSP189 was constructed by and obtained from Dr. Michael Seidman (Otsuka Pharmaceuticals, Bethesda, Md.).

Triplex binding assays. Binding assays were carried out for 2 hours at 37° C. in 10% sucrose, 20 mM $MgCl_2$, 10 mM Tris (pH 8.0), and 1 mM spermidine in a 10 μl volume. The 250 bp supF target was generated from lambda supF using the polymerase chain reaction.

Protection Assay Using PCR Amplified SupF Target

The 250 bp supF target (70 nM) was incubated with a 100-fold molar excess of psoralen-AG10 as described for the binding assay. Irradiation of samples was performed at a dose of 1.8 $J/cm^2$. A radiometer was used to measure the lamp output (typical UVA irradiance of 5–7 $mW/cm^2$ at 320–400 nm). Following the binding and irradiation steps, samples were digested for 2 hours at 37° C. with Hinf I. Loading buffer was added and samples were heated 10 minutes at 55° C., and run for 1 hour on a 4.5% Nusieve gel in TAE buffer at 80 v (10 v/cm).

Protection Assay Using SV40 Vector DNA Target.

The binding and irradiation were carried out as described above, except that pSP189 was used as the supF target at a concentration of 50 nM and psoralen-AG10 was added at ratios of oligomer to vector of from 1:1 to 1000:1. Irradiation and gel conditions were as described above.

Colony hybridization. Ampicillin resistant colonies of SY204 carrying shuttle vector plasmids with supF gene mutations, along with appropriate control colonies, were grown on LB/ampicillin plates and transferred onto replica nylon filters for additional growth and in situ lysis to allow colony hybridization by standard methods. The DNA was fixed to the filters by UV crosslinking, and the filters were incubated in 6×SSC, 5×Denhardt's solution, 0.5% SDS, and $5\times10^5$ cpm/ml of $^{32}$P-labeled oligonucleotides at 42° C. for 18 hours. The filters were washed in 1×SSC and 0.1% SDS for 30 minutes at 25° C. and then in 1×SSC and 0.1% SDS at 42° C. for 2 hours. These conditions were empirically determined to allow discrimination between binding of the wild type probe (5' GGT TCG AAT CCT TCC CCC 3') (SEQ ID NO:6) and the 167 mutant probe (5' GGT TCG AAA CCT TCC CCC 3') (SEQ ID NO:7). Binding of the oligonucleotide probes was determined by autoradiography.

SV40 mutagenesis. The SV40 vector DNA (pSP189) at 80 nM was incubated with psoralen-AG10 or psoralen-GA10 (ranging from 2 to 1000-fold molar excess) and irradiated as described above. The oligonucleotide-plasmid complex was then transfected into monkey COS-7 cells (ATCC #1651-CRL) using cationic liposomes (DOTAP, Boehringer Manheim, Indianapolis, Ind.) at a final concentration of 5 μg/ml in the culture dish. The DNA/oligo/liposome mixture was added dropwise to the cell culture dish with swirling. The following day, the media containing the liposome mixture was replaced by fresh media. Following 48 hours to allow repair and replication, SV40 vector DNA was harvested from the COS cells by the Hirt lysate procedure. Genetic analysis of the supF genes in the SV40 vector was carried out by transformation of *E. coli* SY204 [lacZ125(Am)] to ampicillin resistance by electroporation using 12–150 ng of Dpn I digested Hirt lysate DNA and a Bio-Rad Gene Pulser apparatus equipped with a Pulse Controller (Bio-Rad, Richmond, Calif.). Mutants were identified by growth in the presence of 65 μg/ml IPTG and 80 μg/ml X-Gal, as described by (Glazer et al., *Mol. Cell Biol.* 7:218–224 (1987)). These transformants were counted and the mutants (white colonies) were streaked for single colonies.

DNA Sequencing. DNA was prepared for sequencing by isolating DNA from a 3 ml bacterial culture using a Promega Magic Miniprep kit (Promega, Madison, Wis.). DNA sequence data was obtained by direct chain termination sequencing of the plasmid DNA using automated methods.

Results

Figure 4:
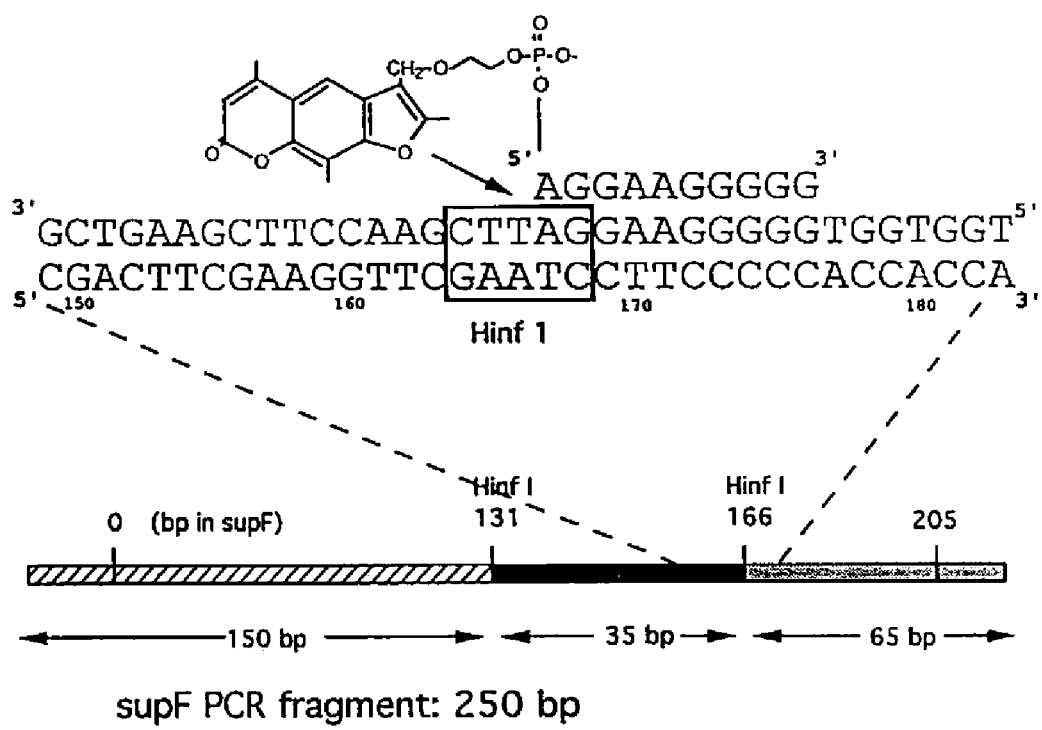
FIG. 4 shows Hinf I digestion and Hinf I digests.

Strategy for Targeted Mutagenesis in SV40. An SV40-based shuttle vector (pS189) was used to assay for targeted mutagenesis. This vector contains both the SV40 and the pBR328 origins of replication, plus the β-lactamase gene for ampicillin resistance, to allow episomal replication in both mammalian cells and bacteria (FIG. 4). It also carries the supF gene, an amber suppressor tyrosine tRNA gene of E. coli, as a marker gene for mutagenesis studies.

In this vector system, the SV40 DNA, after appropriate treatment, is introduced into monkey COS cells where repair and replication can occur, producing mutations indicative of mammalian processing of DNA damage. The small, circular vector DNA is recovered from the cells by biochemical separation from the chromosomal DNA (Hirt lysate, Hirt et al., J. Mol. Biol. 26:365–369 (1967)), and it is used to transform E. coli carrying the lacZ (amber) mutation to allow analysis of supF gene function by scoring colonies for β-galactosidase activity (produced via suppression of the amber mutation in lacZ) in the presence of the chromogenic substrate, X-gal. Vectors with wild type supF genes yield blue colonies; those with mutations in supF produce white ones. In order to eliminate misleading data that might arise from viral DNA that was not replicated or repaired in the mammalian cells, the viral DNA is digested before bacterial transformation with the enzyme Dpn I which will restrict DNA that has not been methylated by the mammalian pattern at its recognition site.

The design of the initial experiments to target mutations to SV40 DNA is illustrated in FIG. 3. A 10 base pair region of the supF gene (bp 167–176) was identified as a site amenable to triplex formation because of the homopurine/homopyrimidine run there. Since this run was G-rich, the purine motif for triplex formation was selected (Beal and Dervan, Science 251:1360–1363 (1991)), and an oligonucleotide, 5'AGGAAGGGGG3' (SEQ ID NO:2) (AG10) was synthesized based on this motif. A psoralen derivative, 4'-hydroxymethyl-4,5',8-trimethylpsoralen, was attached to the oligonucleotide by a phosphodiester linkage at the 5' adenine via a two carbon linker arm, with the goal of directing mutations to base pair 167. This is the base pair with which that 5' adenine binds in the predicted triple helix. Note that the psoralen-AG10 oligonucleotide is oriented anti-parallel to the purine-rich strand in the duplex DNA. To achieve targeted mutagenesis, the pSP189 DNA is incubated with the psoralen-linked oligonucleotide (psoralen-AG10), treated with long wave ultraviolet light (UVA) to activate the psoralen to form a pre-mutagenic adduct on the thymidine in base pair 167, and then transfected into COS-7 cells. After a 48 hour period to allow repair and replication, the viral DNA is isolated from the monkey cells, subjected to digestion with Dpn I, and used to transform E. coli. The frequency of supF mutations is determined, and representative samples of supF mutant clones are collected for further analysis.

Site-specific formation of triplex DNA. This experiment demonstrate the ability of psoralen-AG10 to bind specifically to the intended site within the supF gene using a restriction enzyme protection assay. In this assay, psoralen-AG10 was found to bind site-specifically to duplex supF DNA following UVA irradiation, blocking restriction enzyme digestion at the one Hinf I site (bp 164–168) that overlaps the triplex target site (167–176) but not at the other Hinf I site in supF (bp 129–133). This is diagrammed in FIG. 4. A gel demonstrated site-specific formation of triplex DNA in the supF gene by psoralen-AG10 using a restriction enzyme protection assay. Analysis by agarose gel electrophoresis of Hinf I digestions of the 250 bp supF gene PCR fragment under various conditions was done. The supF fragment was incubated with or without psoralen-AG10 at a 100-fold molar excess, treated by 1.8 J/cm$^2$ of UVA irradiation, and then subjected to Hinf I digestion. Digestion of the unprotected 250 bp supF PCR fragment with Hinf I yielded three fragments of sizes 150, 65, and 35 in contrast with the uncut fragment of 250 bp. Incubation of the supF fragment with psoralen-AG10 along with photoactivation with UVA resulted in protection of the Hinf I site at bp 164–168 but not the one at bp 129–133, as the 100 bp fragment appeared instead of the 65 bp and 35 bp fragments. UVA-induced covalent adduct formation is required for restriction enzyme protection, since psoralen-AG10 alone is not sufficient to prevent Hinf I digestion. In the absence of psoralen-AG10, UVA light had no effect on Hinf I digestion. In similar experiments, no protection from Hinf I cutting was seen using psoralen-GA10, the reverse sequence oligomer linked to psoralen. This data demonstrates site-specific formation of triplex DNA by psoralen-AG10, with covalent modification of the supF gene fragment occurring at the targeted site following UVA irradiation of the psoralen-AG10/supF complex.

Similar experiments were performed to assay for site-specific binding of psoralen-AG10 to bp 167–176 in the supF gene within the SV40 vector itself. In these experiments, varying ratios of oligonucleotide to vector DNA were employed in order to examine basic parameters of the triplex binding to the viral genome. A gel experiment showed site-specific formation of triplex DNA in the SV40 vector as a function of the ratio of oligonucleotide to SV40 DNA. Binding of psoralen-AG10 as a triple strand to bp 167–176 of the supF gene within the SV40 vector was assayed by examining protection from Hinf I digestion at bp 164–168, as diagrammed in FIG. 4. The SV40 vector containing the supF target gene (50 nM) was incubated with psoralen-AG10 at ratios of oligomer to vector of from 1:1 to 1000:1, irradiated with 1.8 J/cm$^2$ of UVA, digested with Hinf I, and run on a 4.5% Nusieve gel. Because the sequences flanking the supF gene in the SV40 DNA differ from those in the PCR fragment, and since there are multiple Hinf I sites in SV40, the pattern of bands is more complex. Hinf I protection at the targeted site is almost complete at a 10:1 ratio of oligonucleotide to vector, as judged by the appearance in the ethidium bromide stained agarose gel of a band at 125 bp and the disappearance of the band at 90 bp. Ratios of 100:1 and 1000:1 similarly yielded near complete protection, whereas the lower ratios of 1:1 and 2:1 gave only partial protection. These results are consistent with the mutagenesis experiments, described below.

Targeted mutagenesis of SV40 vector DNA passaged in COS Cells. Experiments to induce targeted mutagenesis in SV40-vector DNA using triplex-forming oligonucleotides were carried out as shown in FIG. 3. Psoralen-linked oligonucleotides were incubated with SV40 vector DNA, exposed to 1.8 J/m$^2$ UVA light, and transfected into COS cells. After two days to allow repair and replication to occur, the vector DNA was rescued from the cells and used to transform bacteria to facilitate genetic analysis of the supF gene. The effect of psoralen-AG10, which binds site-specifically to the supF gene in the vector, in inducing supF mutations was compared to that of psoralen-GA10, which shows no specific binding. Various ratios of oligonucleotide to vector DNA were used in order to investigate parameters that might affect the specificity and the efficiency of the process of targeted mutagenesis in the monkey cells. Table 2 presents the data from these experiments. Targeted mutations in the supF gene were produced in the SV40 genome at a frequency as high as 7.3% using psoralen-AG10 at a molar ratio of oligonucleotide to vector DNA of 1000 to 1. At this same ratio, psoralen-GA10 produced a small amount of mutagenesis above background (0.5% versus 0.07%). At the lower ratios tested, however, the reverse oligomer yielded no significant mutagenesis above the background frequency in the assay, whereas, at these lower ratios, psoralen-AG10 still generated a high frequency of mutations in supF (as high as 6.4% for the 10:1 ratio versus 0.06% for psoralen-GA10 at 10:1 and 0.07% for untreated vector DNA). This demonstrates mutagenesis specifically targeted to the supF gene in the SV40 vector by psoralen-AG 10 but not by psoralen-GA10. This frequency of targeted mutagenesis in SV40, in the range of 6% to 7%, is 30-fold higher than that seen in previous experiments to target the supF gene in bacteriophage lambda grown in *E. coli* (0.23%, ref. X), and it suggests that-the monkey cells more efficiently process the pre-mutagenic lesion of the psoralen/oligonucleotide adduct into a mutation, via either error-prone repair or bypass replication.

In control experiments (Table 2), UVA irradiation of the SV40 DNA, in the absence of the psoralen-linked oligonucleotides, produced no mutagenesis above background. Similarly, the treatment of the SV40 DNA with the oligomers but without UVA irradiation was not mutagenic.

Sequence analysis of targeted mutations. A set of 20 mutants generated in the supF gene in the SV40 vector by psoralen-AG10 (at the 1000:1 ratio) and UVA light were subjected to DNA sequence analysis. The results of this analysis are shown in FIG. 5A. Of the 20 mutations analyzed, 11 consist of the same T:A to A:T transversion at base pair 167 occurring over and over again. This is the precise base pair to which the mutations were targeted by psoralen-AG10, as diagrammed in FIGS. 5A and 5B. The finding that 55% of the sequenced mutations consisted of the exact same base change at the targeted base pair suggests that the intended base change (T:A to A:T at bp 167) was produced in over 4% of all the viral genomes. The other mutations analyzed included 3 point mutations at base pairs adjacent to the targeted base pair and 6 small deletions including or abutting that base pair. These likely arise from variations in the processing, repair, or replicative by-pass of the triplex-directed lesion at bp 167 as the SV40 DNA is replicated in the monkey cells. It is also possible that the psoralen molecule, tethered to the oligonucleotide by a 2-carbon linker arm, has sufficient reach and degrees of freedom to form adducts at nearby base pairs. Improved mutational specificity may be achieved by reducing the length of the linker arm. In FIG. 5B, the published sequences of supF mutations produced in this same vector system using free 8-methoxypsoralen are presented for comparison. Not only are these mutations more scattered, but also none were found to occur at base pair 167.

In the analysis of mutagenesis in SV40 vectors, it is often difficult to determine if identical mutations arose independently or if they were the result of a single mutational event amplified by subsequent vector replication. In order to exclude the possibility that such sibling mutations were isolated in these experiments, use was made of an advantageous feature of the pSP189 system, in which over 100,000 different, random-sequence 8 base pair oligonucleotides were cloned into a region of pSP189 next to the supF gene. The vector DNA is prepared en masse from this library of vector clones containing the different 8 bp sequences. In this way, at the same time that the sequence of the supF gene in a mutant vector is ascertained, the 8 base pair signature sequence in that particular plasmid molecule can also be identified by reading a few extra bases further in the sequence data. This enables comparisons between the 8 bp signature sequences in plasmids bearing the same supF mutation to see if they are siblings from the same mutational event or if they are independent mutations. Based on this analysis, it was determined that all 20 of the mutations presented here arose independently.

In order to strengthen and confirm these results, a larger sample of supF mutations produced in the SV40 vector by psoralen-AG10 and UVA light was analyzed by an alternate method based on the expected high proportion of T:A to A:T transversions at bp 167. Instead of direct sequencing, a technique of differential oligonucleotide hybridizations was used (Sidransky et al., Science 252:706–709 (1991)). In this assay, undertaken in an effort to streamline mutant analysis, ampicillin resistant bacterial colonies containing mutant supF genes were grown on nylon filters to allow nucleic acid hybridizations. Duplicate filters were incubated with $^{32}$P-labelled, 18 base oligonucleotides that either matched the wild type sequence or matched the position 167 T:A to A:T mutant sequence. The hybridizations were carried out by standard methods under conditions empirically determined to be stringent enough to allow differentiation between mutant and wild type sequences. An analysis was done of supF gene mutations in the SV40 vector by a colony hybridization assay. Bacterial colonies containing SV40 plasmid vector DNA carrying supF gene mutations were grown and lysed in situ on nylon filters to allow nucleic acid hybridization. Oligonucleotide probes that either exactly matched the wild type sequence of the supF gene at base pairs 158–176 or matched the sequence of the 167 T:A to A:T transversion mutation at those base pairs were radioactively labeled and allowed to hybridize with duplicate filters under conditions designed to enable discrimination between mutant and wild type sequences. Binding was visualized by autoradiography. Results showed in this particular experiment that of the 19 colonies assayed, 9 showed hybridization specific to the mutant probe. None showed hybridization to the wild type probe, except for the positive control. For the 9 colonies that bind to the 167 probe, this supports the validity of the assay. For the other 10 that did not bind to the mutant probe either, the lack of binding to the wild type probe suggests that they either have different mutations at bp 167 (not T:A to A:T) or have mutations near bp 167, within the 18 bp region covered by the probes, causing mismatches with both the wild type and mutant oligonucleotides. A total of 42 mutants generated by psoralen-AG10 were analyzed by this method (including the 20 subject to sequence analysis), and 22 (52%) were found to carry the T:A to A:T mutation at bp 167. All of the rest were judged to have different mutations at or near the targeted base pair, because neither the mutant nor wild type probe hybridized to them. The validity of this assay was supported by the 100% agreement with the sequencing data. These results extend the direct sequencing data and demonstrate further the targeted mutagenesis of SV40 vector DNA. Taken together, the data suggests that almost all of the mutations produced by psoralen-AG10 are at or within a few bases of the targeted base pair, and at least 50% consist of the same T:A to A:T transversion at that site. These results demonstrate efficient production of specific, reproducible, and predictable mutations at a targeted base pair in SV40 DNA passaged in monkey cells.

TABLE 2

Targeted mutagenesis in SV40 DNA

| Treatment of SV40 vector DNA[a] | Ratio of oligo to vector | % mutants[b] | Mutants per total colonies |
|---|---|---|---|
| None | n.a. | 0.07 | 6/8,190 |
| psoralen-AG10[c] no UVA | 1000:1 | ≦0.06 | 0/1700 |
| psoralen-GA10[c] no UVA | 1000:1 | ≦0.07 | 0/1500 |
| UVA alone | n.a. | 0.06 | 5/8,427 |
| psoralen-AG10[c] | 2:1 | 2.5 | 148/5,869 |
|  | 5:1 | 4.3 | 118/2,734 |
|  | 10:1 | 6.4 | 381/5,995 |
|  | 1000:1 | 7.3 | 633/8,643 |
| psoralen-GA10[c] | 2:1 | 0.07 | 3/4,397 |
|  | 5:1 | 0.13 | 11/8,230 |
|  | 10:1 | 0.06 | 4/6,800 |
|  | 1000:1 | 0.63 | 92/14,670 |

[a]Except where indicated, all samples received 1.8 J/cm² of UVA irradiation.
[b]The values represent the frequency of mutations seen in the supF gene within the pSP189 SV40 vector.
[c]Psoralen-AG10 forms a site-specific triple strand at bp 167–176 of the supF gene within pSP189; the reverse sequence oligomer, psoralen-GA10, does not.

EXAMPLE 5

Targeted Mutagenesis in Mouse Fibroblasts

For the purposes of achieving targeted mutagenesis in mouse cells in vivo, the assay system to detect mutations in the chromosomes of mouse fibroblasts in culture developed by Glazer et al. was used (*Proc. Natl. Acad. Sci. USA* 83:1041–1044, (1986), which is incorporated by reference herein). This system allows detection and analysis of mutations occurring in the supF gene contained within the chromosomes of the LN12 cells, a derivative of mouse L cells into whose chromosomes multiple copies of the lambda supF shuttle vector were inserted.

Figure 6:
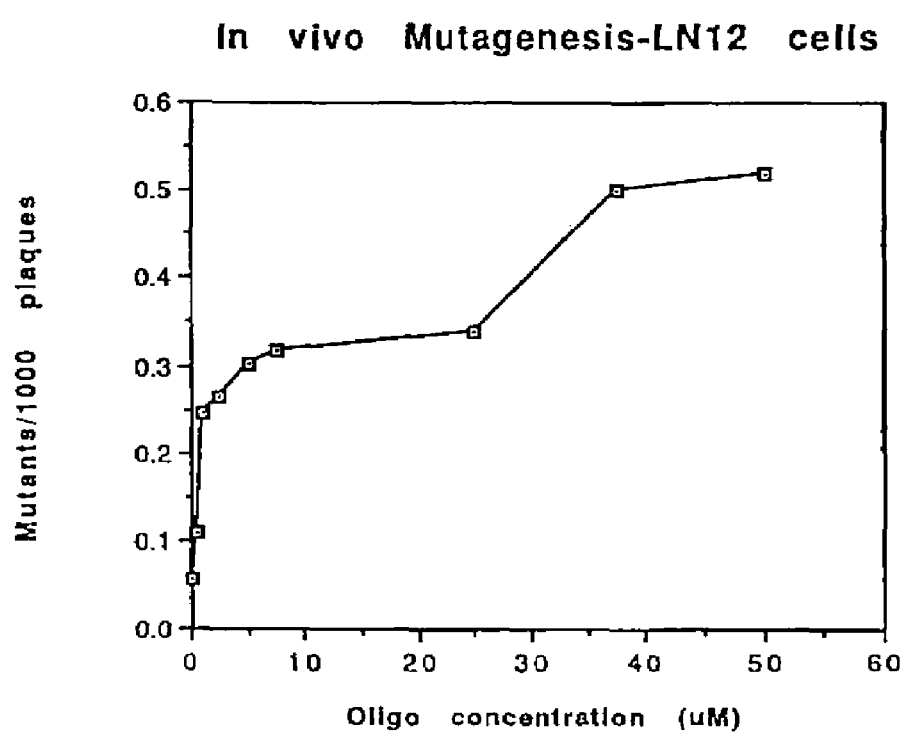
FIG. 6 is a graph of in vivo mutagenesis of monkey fibroblast LN12 cells showing oligonucleotide concentration versus mutants per 1000 plaques.
Figure 7:
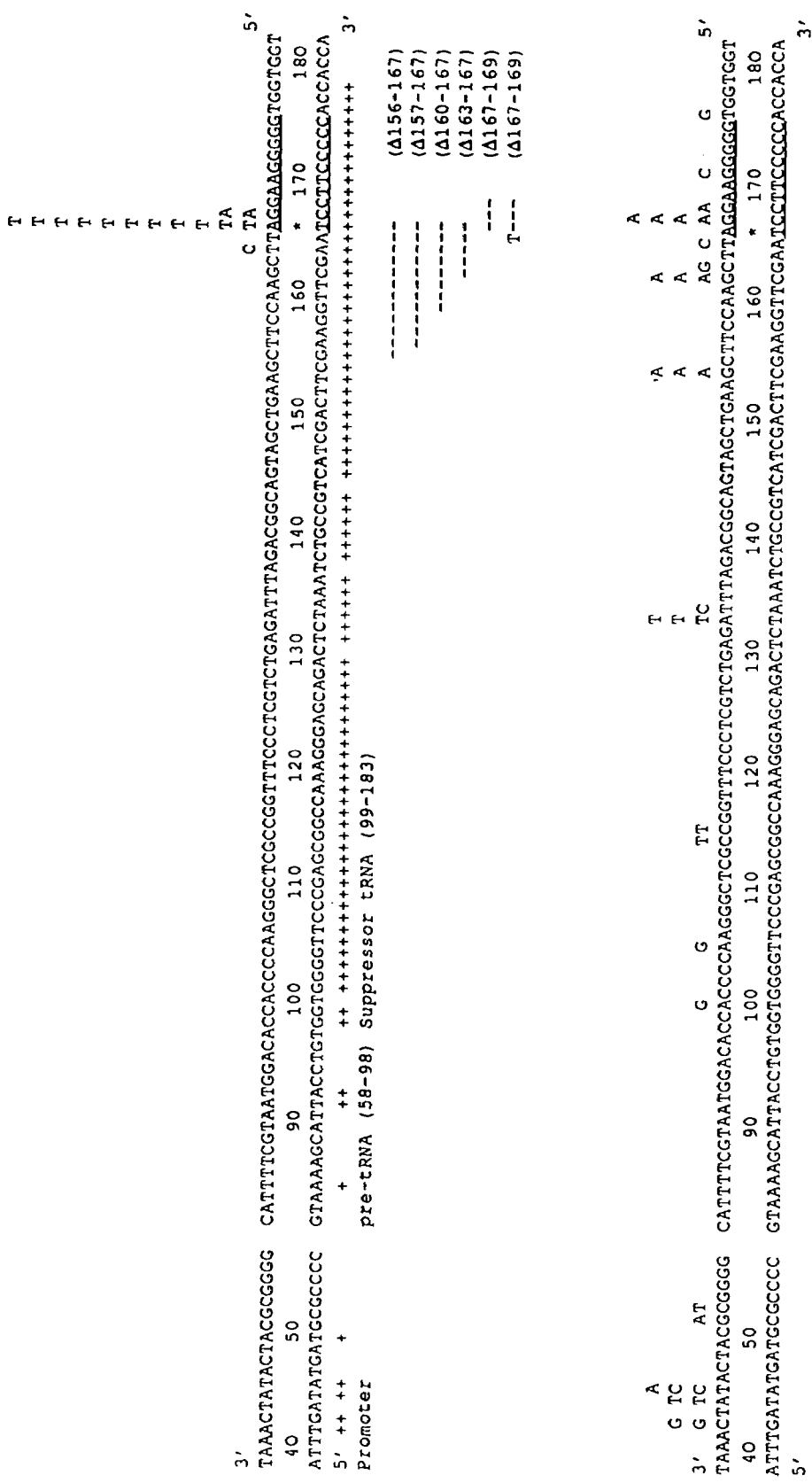
Figure 8:
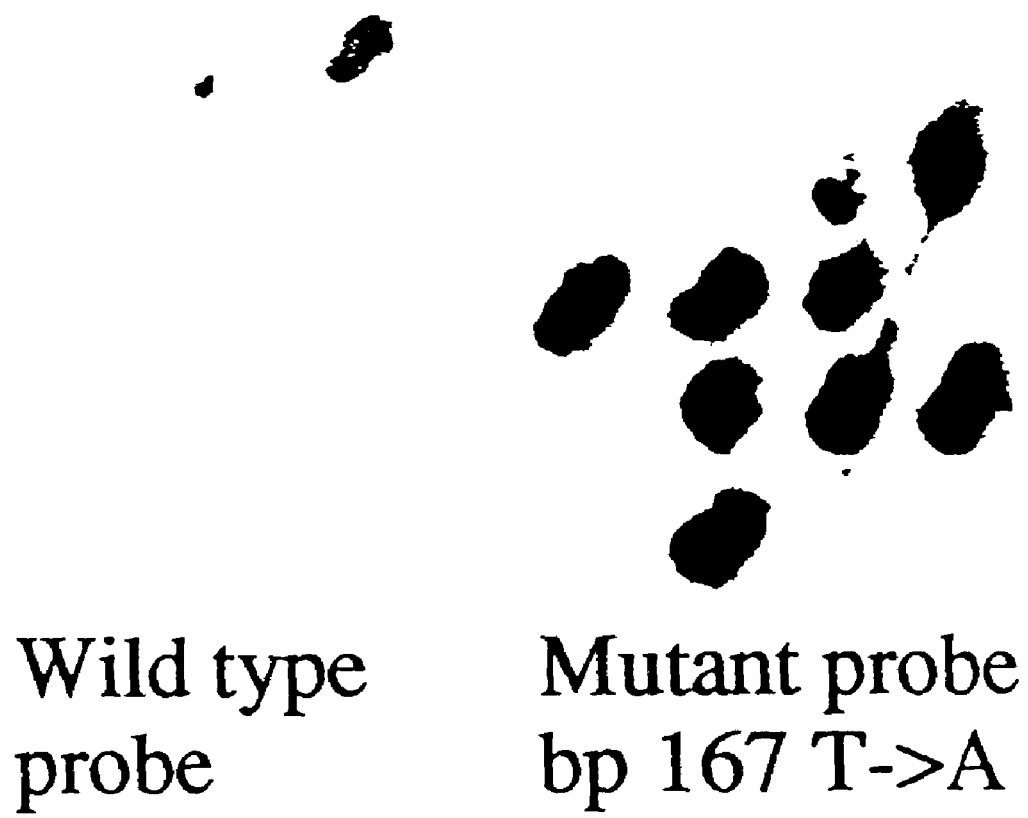
Figure 9:
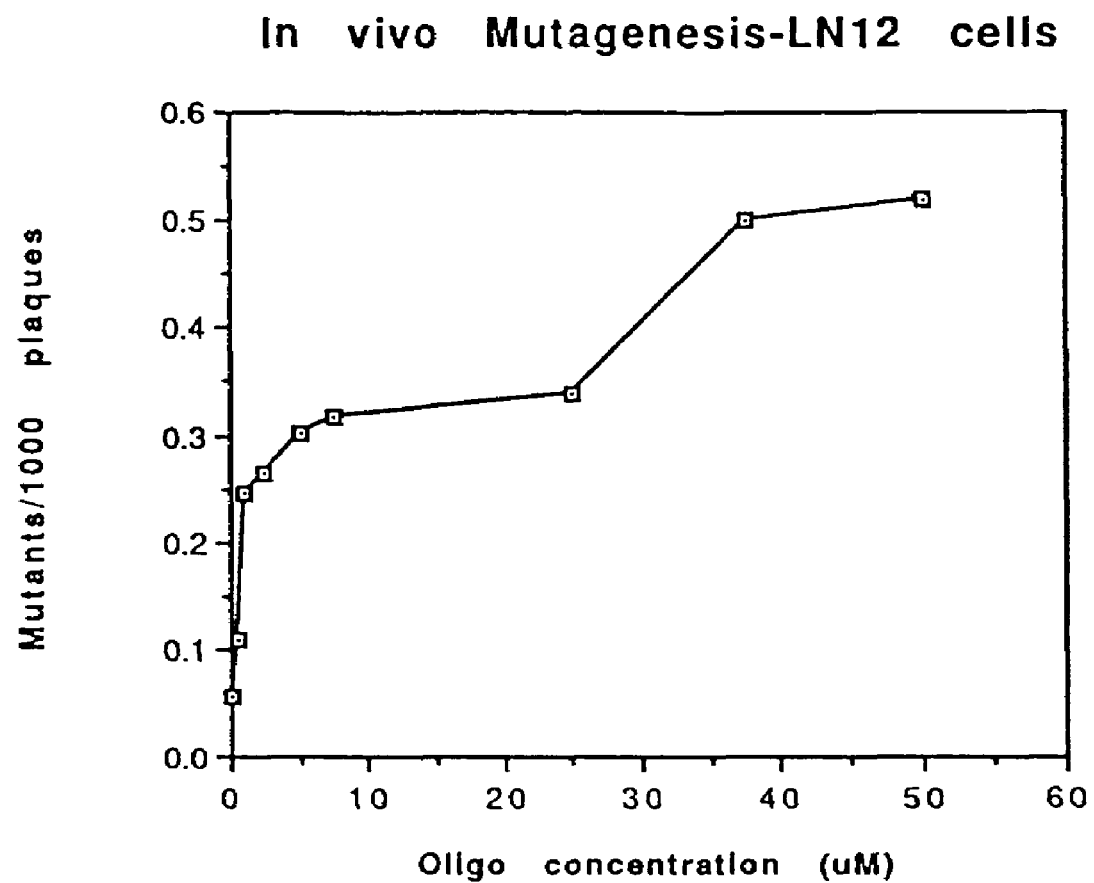

The LN12 cells, growing in culture, were treated with the oligonucleotide, psoralen-AG10, which is designed to target mutations to base pair 167 in the supF gene via sequence-specific triplex formation and thereby delivery of the psoralen to that site. This oligonucleotide was used also in the lambda and the SV40 experiments. The oligonucleotide was added directly to the growth medium of the cells at various concentrations in the range of 0.1 to 50 μM. Two hours later, the cells were exposed to 0.07 J/cm² of UVA irradiation, the cells were allowed to grow for an additional 2 to 4 days, and then DNA was prepared from the cells to analyze for mutations in the supF gene. Using lambda in vitro packaging extracts to rescue the supF gene in the lambda vector from within the mouse DNA (as described by Glazer et al., cited above), mutations were detected in approximately 0.05% of the supF genes. Over forty mutant supF genes have been isolated in these recent experiments (from all concentrations of oligonucleotide studied), but the sequence of only one has been determined so far. This mutation was a T:A to A:T transversion exactly at the targeted base pair, precisely as intended by use of the psoralen-AG10 oligonucleotide, and consistent with the results in targeting the lambda and SV40 genomes. There was a dose-response relationship seen in the induction of supF mutations, with a higher frequency seen as the concentration of oligonucleotide to which the cells were exposed was increased as shown in FIG. 6.

This preliminary data demonstrates that this approach of using chemically-modified, triplex-forming oligonucleotides linked to mutagenic chemicals can target mutations to one specific base pair out of the entire genome of living mammalian cell.

Modifications and variations of the present invention, mutagenic triplex-forming oligonucleotides, as well as methods of use thereof, will be obvious to those skilled in the art from the foregoing detailed description. Such modifications and variations are intended to come within the scope of the appended claims.

We claimed:

1. A method for site-directed mutagenesis of a nucleic acid molecule comprising the steps of:
   a) hybridizing a mutagenic oligonucleotide to a target region of a double-stranded nucleic acid molecule, wherein the mutagenic oligonucleotide comprises a mutagen incorporated into a single-stranded nucleic acid that forms a triple-stranded nucleic acid molecule with the target region; and
   b) mutating the double-stranded nucleic acid molecule.

2. The method of claim 1 comprising the additional step of activating the mutagen prior to the mutation step.

3. The method of claim 1 wherein the mutagen is selected from the group consisting of psoralen and acridine orange and is activated by light.

4. The method of claim 1 wherein the mutagen is selected from the group consisting of acridine orange, an alkylating agent, a cis-platinum analog, a hematoporphyrin, a hematoporphyrin derivative, mitomycin C, a radionuclide, and a molecule that interacts with radiation to become mutagenic.

5. The method of claim 1 wherein the mutation alters the activity of the double-stranded nucleic acid molecule.

6. The method of claim 1 wherein the double-stranded nucleic acid molecule is a gene.

7. The method of claim 1 wherein the gene is an oncogene.

8. The method of claim 1 wherein the gene is a defective gene.

9. The method of claim 1 wherein the double-stranded nucleic acid molecule is all or a portion of a viral genome.

* * * * *